United States Patent [19]

Kervennal et al.

[11] 4,454,322
[45] Jun. 12, 1984

[54] PROCESS FOR THE PREPARATION OF 2-BENZOXAZOLONE AND DERIVATIVES FROM ORTHO-NITROPHENOLS AND CARBON MONOXIDE

[75] Inventors: Jacques Kervennal, Lyons; Jean-Marie Cognion, Saint Genis Laval; Pierre Durual, Vernaison, all of France

[73] Assignee: Atochem, Paris, France

[21] Appl. No.: 460,431

[22] Filed: Jan. 24, 1983

[30] Foreign Application Priority Data

Feb. 23, 1982 [FR] France ............................... 82 02921

[51] Int. Cl.³ ................... C07D 498/00; C07D 263/54
[52] U.S. Cl. .................................. 548/221; 548/219; 260/689
[58] Field of Search ................. 548/219, 221; 260/689

[56] References Cited

U.S. PATENT DOCUMENTS

| | | | |
|---|---|---|---|
| 3,523,964 | 8/1970 | Kober et al. | 260/689 |
| 3,657,265 | 4/1972 | Kober et al. | 548/219 |
| 3,678,042 | 7/1972 | Matter | 548/219 |
| 3,832,401 | 8/1974 | Knifton et al. | 260/689 |

FOREIGN PATENT DOCUMENTS

34875 5/1973 Japan ................................. 548/219

OTHER PUBLICATIONS

Manov-Yuvenskii et al., Uzb. Khim. Zh., (4), 26–29, (1980).

Nefedov, B. K., et al., Izv. Akad. Nauk. SSSR, (7), 1555–1559, (1977).

*Primary Examiner*—Mary C. Lee
*Assistant Examiner*—S. A. Gibson
*Attorney, Agent, or Firm*—Beveridge, DeGrandi & Kline

[57] ABSTRACT

Process for the preparation of 2-benzoxazolone and derivatives by the reaction, in the liquid phase, at a temperature from 100° to 500° C. and a pressure from 20 to 500 bars, of an ortho-nitrophenol of the formula:

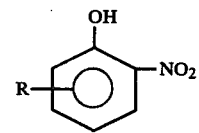

in which R represents a hydrogen or halogen atom, an alkyl group containing from 1 to 10 carbon atoms or an alkoxy group OR' in which R' represents an alkyl group containing from 1 to 10 carbon atoms, and carbon monoxide under pressure, characterized in that the process is carried out in the presence of
 a. a supported catalyst formed by the association of a noble metal of Group VIII and a second transition metal selected from Groups, $V_b$, $VI_b$ or VIII of the Periodic Classification, in the metallic or oxide form, and
 b. a nitrogenous heteroaromatic base; the process may be carried out in the presence of a solvent.

17 Claims, No Drawings

PROCESS FOR THE PREPARATION OF 2-BENZOXAZOLONE AND DERIVATIVES FROM ORTHO-NITROPHENOLS AND CARBON MONOXIDE

The present invention relates to a process for the preparation of 2-benzoxazolone and derivatives by reaction in the presence of a nitrogenous heteroaromatic base, of ortho-nitrophenols with carbon monoxide under elevated pressure, and in the presence of supported catalysts consisting of a noble metal and another transition metal deposited in the form of metallic particles or oxides.

2-benzoxazolone is an intermediate used in fine chemistry, particularly in the development of certain colorants. The classical synthesis from ortho-nitrophenol requires two stages, the first being hydrogenation to orthoaminophenol, and the second, phosgenation. There are multiple disadvantages in the use of phosgene; these include the need to synthesize and manipulate this dangerous product, and the by-production of significant amounts of hydrochloric acid which makes it necessary to carry out a reaction which uses it up, or to electrolyze it, which in turn requires the installation and costly maintenance of an additional plant. The development of a process which allows the use of phosgene to be avoided, and permits the synthesis of 2-benzoxazolone in a single stage, is therefore of definite interest.

Amongst possible syntheses, the reaction of carbon monoxide on ortho-nitrophenol according to the following reaction scheme:

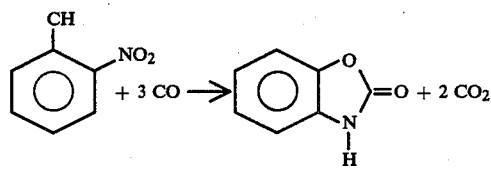

has already been described in Japanese Pat. No. 34 875/73. This synthesis is carried out in the presence of a halide of a metal of the platinum group, associated with a metal oxide from Groups $V_b$, $VI_b$ or VIII of the Periodic Classification, without disclosure of any details on the recovery and recycling of the catalyst. However, such systems in which the composition and the exact structure are inadequately defined, require high concentrations of catalyst in order to obtain proper reaction speeds.

It has now been discovered that catalytic systems formed from a noble metal and a second transition metal present in the form of metallic crystallites or oxides deposited on a support, associated with a nitrogenous heteroaromatic base, have proved to be particularly selective and exhibit increased activity in the carbonylation of ortho-nitrophenols into 2-benzoxazolones.

The process according to the invention is applicable to molecules of orthonitrophenols with the formula:

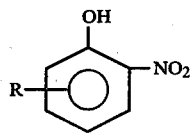

in which R represents a hydrogen or halogen atom, an alkyl group containing from 1 to 10 carbon atoms, or alkoxy group $OR'$ in which $R'$ represents an alkyl group having from 1 to 10 carbon atoms.

The technique according to the invention consists in associating on the support, a noble metal of Group VIII of the Periodic Classification with a second transition metal selected from Groups $V_b$, $VI_b$ or VIII and present in the form of metallic particles or oxides.

Among the couples which can be favorably associated, are included, in a non-limiting fashion, the following system: palladium-molybdenum, palladium-iron, palladium-vanadium, platinum-molybdenum and platinum-iron.

The metals or oxides can be deposited on different supports made from various mineral or organometallic compounds according to known techniques of impregnation to give, after appropriate treatment, catalysts to be used in the invention. The metallic compounds may be introduced one after the other, but is is preferable to impregnate them simultaneously. Thus, the support, under a nitrogen atmosphere, can be covered with a solution of metallic derivatives in an organic solvent or in water, and then the whole is degassed under vacuum and the solvent distiled off.

According to another method of operation, the support is placed in a constantly rotating flask, regularly agitated and a solution of the metallic derivatives is sprinkled in under conditions of temperature and pressure such that the solvent is evaporated in proportion to its introduction.

Among metallic precursors which can be used are the acetates, nitrates, halides or organo-metallic complexes of the noble metals; the acetates, nitrates, halides or oxalates of other transition metals, but also mixed salts such as, for example, ammonium molybdate, or heteropolymetallic molecular complexes which directly associate the couples cited above; mixed clusters are good examples of such molecular species.

The impregnated support, after drying, is brought to at least 300° C. under nitrogen, with the aid of a linear temperature program at the rate of 2° C./min. in order to decompose the precursors into metallic crystallites or oxides active in the reaction studied.

The supports which can be used are varied; in a non-limiting fashion there are disclosed aluminas, silicas, silica-aluminas, magnesia, active charcoal and silicon carbides.

The impregnation can be carried out in a manner such as to give amounts of noble metal on the support varying from 0.1 to 20% by weight, but preferably from 1 to 15%. The ratio of the number of gram-atoms of the second metal in relation to that of the noble metal varies from $10^{-2}$ to $10^2$, and is preferably from 0.1 to 10.

According to the process of the invention, the nitrophenol is put in contact with the carbon oxide at elevated temperature and pressure in the presence of the catalyst deposited on a support and of a nitrogenous heteroaromatic base such as pyridine or quinoline. The presence of a nitrogenous heteroaromatic base in the reaction medium improves the activity and selectivity of the catalyst. It is added to the reaction medium in amounts from $10^{-2}$ to 30 moles per mole of nitro derivative, preferably from 0.1 to 10 moles per mole thereof.

The concentration of the catalyst in the reaction medium, expressed by the ratio of the number of gram-atoms of noble metal to the number of nitro groups to be converted, varies from $10^{-4}$ to 1, and is preferably from $5.10^{-3}$ to $10^{-1}$.

The reaction may be conducted in the absence of solvent, working in molten o-nitrophenol, but dilution in a solvent may favor selectivity. The preferred solvents used are saturated hydrocarbons containing from 6 to 12 carbon atoms such as hexane, heptane, n-decane or decalin, aromatic hydrocarbons containing from 6 to 12 carbon atoms such as benzene, toluene or xylene, aromatic halides such as chlorobenzene and the dichlorobenzenes, or nitrogenous heterocyclics wherein the heterocycles contain from 3 to 5 carbon atoms such as pyridine or bipyridine, or equally, fluorinated solvents can be used, such as perfluorinated methyldecalin or trichlorotrifluoroethane.

When operating in the presence of solvent, the proportion is not critical, but generally preferred are solutions containing 5 to 50% by weight of the nitro derivative in the solvent.

The reaction temperatures are between 100° and 500° C., and more particularly between 150° and 250° C.

The pressures are between 20 and 500 bars and preferably between 100 and 350 bars.

It is possible to operate with a discontinuous technique in an autoclave-type apparatus, or with a continuous technique which permits elimination of the benzoxazolone product as it is formed.

Because of the fact that they are insoluble in the reaction medium, the catalysts are easily recovered after reaction by simple filtration and their stability allows them to be recycled without loss of activity.

The tests described in the following examples have been carried out in a discontinuous manner in a Hastelloy C autoclave, with 500 ml capacity and fitted with a magnetic stirring device, which can operate under pressures up to 500 bars and temperatures of 300° C. The autoclave, charged with an ortho-nitrophenol, a heteroaromatic base, any solvent and the catalyst, is then swept with nitrogen before being put under pressure with the carbon oxide at normal temperature. It is then heated to the chosen temperature and the progress of the reaction is controlled by recordal of the pressure. After reaction, the amount of any residual nitrophenol and the benzoxazolone formed are determined by liquid chromatography under pressure.

The results indicated are to be understood in relation to the following definitions:

T.T.G. total conversion rate =

$$\frac{\text{number of moles of nitrophenol converted}}{\text{number of moles of nitrophenol introduced}} \times 100$$

Selectivity for benzoxazolone:

$$\frac{\text{number of moles of benzoxazolone formed}}{\text{number of moles of nitrophenol converted}} \times 100$$

Yield of benzoxazolone:

$$\frac{\text{number of moles of benzoxazolone formed}}{\text{number of moles of nitrophenol introduced}} \times 100$$

EXAMPLE 1

10 g of a pure alumina, marketed by CONDEA CHEMIE, with a specific surface of 250 m²/g and ground into 200 to 600 μm particles, were placed in a 50 ml flask mounted on an evaporator. The support was allowed to degas for fifteen minutes under a partial pressure of 100 mm of mercury. Then, 170 ml of an aqueous ammoniacal solution containing 1.05 g of palladium acetate and 0.92 g of ammonium molybdate were introduced, drop-by-drop, onto the agitated support, while adjusting the temperature of the oil bath of the evaporator so that the distillation of the solvent was instantaneous. After introduction of all the solution, the impregnated dried support was transferred into a combustion tube swept with nitrogen, the temperature of which was progressively increased at a rate of 2° C./min. up to 300° C. After a period of 20 hours at this temperature, a current of hydrogen was passed for 20 minutes, and then cooling was carried out under nitrogen. Analysis indicated a palladium content of 4.8% and a molybdenum content of 5.8%.

2.22 g of previously-prepared catalyst was placed in a 500 ml Hastelloy C autoclave together with 13.9 g of orthonitrophenol (0.1 mole), 1 g of pyridine and the total volume made up to 100 ml with ortho-dichlorobenzene. After sweeping with nitrogen, compression was applied with carbon monoxide until the pressure reached 200 bars at 20° C. The autoclave was insulated and heated, with stirring, up to 200° C. for 1 hour and 40 minutes. It was then cooled and the reaction mixture recovered. After the catalyst had been recovered by filtration, the solvent was evaporated to dryness and 13.5 g of dark grey residue were obtained, the infra-red spectrum of which corresponded to that of 2-benzoxazolone. Chromatographic analysis showed that the T.T.G. of nitrophenol was 100% and the selectivity for crude 2-benzoxazolone (M.P.=138° C.) was 100%.

After recrystallization from hot water, the melting point was 140° C., and the percentage analysis of the product was as follows.

|  | % C | % H | % N |
|---|---|---|---|
| Theoretical | 62.22 | 3.70 | 10.37 |
| Found | 62.02 | 3.71 | 10.11 |

Comparative Tests

Test A The 500 ml Hastelloy C autoclave was charged with 13.9 g of ortho-nitrophenol, 2.22 g of previously-prepared catalyst and the total volume made up to 100 ml with ortho-dichlorobenzene. After sweeping with nitrogen, carbon monoxide was introduced to give a pressure of 200 bars and the temperature was brought to 200° C. After 1 hour of induction, the pressure reduced slowly and stabilized after 5 hours reaction. After cooling and distilling the reaction mixture to dryness, it was analyzed. The T.T.G. was 97% and the selectivity for crude 2-benzoxazolone was 91%.

Test B The Hastelloy C autoclave was charged with 13.9 g of ortho-nitrophenol, 2.1 g of a 5% palladium on alumina catalyst marketed by the company ENGELHARD (the alumina support has a specific surface above 100 m²/g), 1 g of pyridine, and the volume made up to 100 ml with ortho-dichlorobenzene. Operating as described in the Example 1, the total pressure was raised to 200 bars at normal temperature by means of carbon monoxide and then it was heated to 300° C. After 1 hour of induction without consumption, the reaction was allowed to proceed for 4½ hours. The reaction mixture was then analyzed at the reactor outlet. The T.T.G. was 100% and the selectivity for 2-benzoxazolone was 89.5%.

EXAMPLE 2

Using the technique described in Example 1, 10 g of pure alumina marketed by CONDEA CHEMIE was successively impregnated with 0.92 g of ammonium molybdate and then 0.97 g of palladium acetate. After the thermal treatment, a catalyst was obtained in which the determined amounts of palladium and molybdenum were 3.5% and 4.5% respectively.

13.9 g of ortho-nitrophenol, 1 g of pyridine and 3 g of catalyst were introduced into the autoclave used in Example 1, and the volume made up to 100 ml with ortho-dichlorobenzene. Adjusting the pressure in the reactor to 200 bars by means of carbon monoxide, the temperature was raised to 200° C. and reaction allowed to proceed for 2¼ hours. After cooling and expansion, the mixture was analyzed. The T.T.G. for nitrophenol was 100% and the selectivity for 2-benzoxazolone was 91%.

EXAMPLE 3

13.9 g of ortho-nitrophenol, 3 g of catalyst prepared as for Example 2, and 1 g of pyridine were introduced into the autoclave and the volume of the charge was made up to 100 ml using ortho-dichlorobenzene. Compression was applied by means of carbon monoxide to 100 bars in this case, and then heating was carried out to 200° C. Reaction was allowed to proceed for 5½ hours, and then cooling, expansion and analysis of the reaction mixture was carried out. The T.T.G. was 93.5% and selectivity for benzoxazolone was 98%.

EXAMPLE 4

A mixed catalyst based on palladium and molybdenum was prepared according to the method described in Example 1. The respective amounts of palladium and molybdenum as indicated by analysis were 4.7% and 4.2%.

13.9 g of ortho-nitrophenol, 2.3 g of catalyst and 1 g of pyridine were introduced into the autoclave and the volume made up to 100 ml with ortho-dichlorobenzene. The pressure was adjusted to 200 bars in the cold with carbon monoxide and then heating was carried out to 200° C. After 1 hour and 50 minutes reaction time, the reactor was cooled, emptied, the catalyst recovered by filtration and the reaction mixture analyzed. The T.T.G. was 100% and the selectivity for benzoxazolone was 100%.

EXAMPLE 5

The 2.3 g of catalyst recovered in Example 4 were recycled in the reactor with 13.3 g of ortho-nitrophenol, 1 g of pyridine and ortho-dichlorobenzene as solvent (quantity sufficient for 100 ml) so that the total volume was 100 ml. The operation was carried out under the same conditions as in Example 4 with 200 bars of pressure with carbon monoxide and to 200° C. The reaction was also allowed to proceed for 1 hour and 50 minutes and the contents of the reactor then analyzed. The T.T.G. of ortho-nitrophenol was 100% and the selectivity for 2-benzoxazolone 100%. Therefore no reduction in the activity or the selectivity of the catalyst was evident after recycling.

EXAMPLE 6

Using the technique described in Example 1, 10 g of pure alumina marketed by CONDEA CHEMIE was simultaneously impregnated with an aqueous solution containing 1.05 g of palladium acetate and 2.07 g of ferric oxalate pentahydrate. After the thermal treatment, a catalyst was obtainedd in which the determined amounts of palladium and iron were 4.6% and 4.0% respectively.

13.9 g of ortho-nitrophenol, 1 g of pyridine and 2.1 g of catalyst were introduced into the autoclave used in Example 1 and the volume made up to 100 ml with ortho-dichlorobenzene. Operating under the conditions stated in the previous examples, the total pressure was brought to 200 bars at normal temperature by means of carbon monoxide and then heating was carried out to 200° C. The reaction was allowed to proceed for 2¼ hours and then the reactor was cooled and the mixture analyzed. The T.T.G. for nitrophenol was 92% and the selectivity for 2-benzoxazolone was 95.6%.

EXAMPLE 7

15 g of 4-chloro 2-nitrophenol, 1 g of pyridine and 1.98 g of catalyst prepared as for Example 4 were introduced into the autoclave and the volume of the charge was made up to 100 ml using ortho-dichlorobenzene. Compression was applied by means of carbon monoxide to 200 bars and then heating was carried out to 200° C. Reaction was allowed to proceed for 1 hour and 30 minutes and then cooling, expansion and analysis of the reaction mixture was carried out. 13.2 g of 5-chloro 2-benzoxazolone were obtained (Rdt 90%).

After recrystallization from hot water, the melting point was 188° C. and the percentage analysis of the product was as follows:

|  | % C | % H | % N | % Cl |
| --- | --- | --- | --- | --- |
| Theoretical | 49.58 | 2.38 | 8.26 | 20.91 |
| Found | 50.67 | 2.34 | 8.24 | 20.92 |

EXAMPLE 8

4 g of commercial alumina, having a particle granulometry of between 200 and 600 μm and a specific surface of 350 m²g/, was impregnated with a solution of 1 g of the mixed cluster $Pd_2Cr_2$ $(\eta^5-C_5H_5)_2$-$(CO)_6(PPh_3)_2$ in methylene chloride. The cluster was prepared according to the operating method by P. BRAUNSTEIN and al. in Angew. Chem. Int. Ed. Engl., 1978, 17, 596 and R. BENDER and P. BRAUNSTEIN in J.Organometallic Chem. 172 (1979) $C_{51}$–$C_{54}$. After heat treatment at 350° C., analysis indicates that the catalyst thus prepared contains 4% of palladium and 1,9% of chromium.

6.9 g of ortho-nitrophenol, 1.48 g of the above catalyst, and 0.7 g of pyridine are placed into the autoclave and the total volume made up to 100 ml with the addition of orthodichlorobenzene. After introduction of carbon monoxide at 200 bars, the autoclave is heated to 200° C., under agitation, for 3 hours. Cooling is allowed to take place and the mixture is analysed. The T.T.G. of orthonitrophenol amounts to 28% and the benzoxazolone-2 selectivity to 94%.

What is claimed is:

1. A process for the preparation of 2-benzoxazolone and derivatives thereof which comprises reacting, in the liquid phase, at a temperature from 100° to 500° C. and a pressure of 20 to 500 bars, an ortho-nitrophenol of the formula:

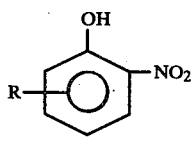

in which R represents hydrogen or halogen, alkyl containing from 1 to 10 carbon atoms, alkoxy in which the alkyl group contains from 1 to 10 carbon atoms, and carbon monoxide under pressure, the process being carried out in the presence of:
- a. a supported catalyst formed by the association of a noble metal of Group VIII and a second transition metal selected from Groups $V_b$, $VI_b$ or VIII of the Periodic Classification, in the metallic or oxide form; and
- b. a nitrogenous heteroaromatic base.

2. The process according to claim 1 in which the concentration by weight of the noble metal on the support varies from 0.1 to 20% by weight.

3. The process according to claim 1 in which the concentration by weight of the noble metal on the support varies from 1 to 15%.

4. The process according to claim 1 in which the atomic ratio of the second metal to the noble metal varies from $10^{-2}$ to $10^2$.

5. The process according to claim 1 in which the atomic ratio of the second metal to the noble metal varies from 0.1 to 10.

6. The process according to claim 1 in which the concentration of the catalyst in the reaction medium, expressed as the ratio of the number of gram-atoms of noble metal to the number of nitro groups to be converted, varies from $10^{-4}$ to 1.

7. The process according to claim 1 in which the concentration of the catalyst in the reaction medium, expressed as the ratio of the number of gram-atoms of noble metal to the number of nitro groups to be converted, varies from $5.10^{-3}$ to $10^{-1}$.

8. The process according to claim 1 in which the nitrogenous heteroaromatic base is introduced at concentrations from $10^{-2}$ to 30 moles per mole of nitro derivative.

9. The process according to claim 1 in which the nitrogenous heteroaromatic base is introduced at concentrations from 0.1 to 10 moles per mole of nitro derivative.

10. The process according to claim 1 in which the nitrogenous heteroaromatic base is pyridine or quinoline.

11. The process according to claim 1 in which the noble metal is palladium and the second transition metal is molybdenum.

12. The process according to claim 1 in which the process is carried out in the presence of a solvent.

13. The process according to claim 12 in which solutions containing 5 to 50% by weight of nitro derivative in the solvent are used.

14. The process according to claim 12 in which the solvent is a saturated or aromatic hydrocarbon selected from hexane, heptane, n-decane, decalin, benzene, toluene and xylene; an aromatic halide selected from chlorobenzene and its dichloro derivatives; a nitrogenous heterocyclic selected from pyridine and bipyridine; a fluorinated solvent selected from perfluorinated methyl decalin and trichlorotrifluoro ethane.

15. The process according to claim 14 in which solutions containing 5 to 50% by weight of nitro derivative in the solvent are used.

16. Process according to claim 1 in which the catalyst supports are aluminas, silicas, silica-aluminas, magnesia, active charcoal or silicon carbides.

17. The process according to claim 12 in which the solvent is a saturated hydrocarbon containing from 6 to 12 carbon atoms, an aromatic hydrocarbon containing from 6 to 12 carbon atoms, an aromatic halide, a nitrogenous hetrocyclic wherein the heterocycles contain from 3 to 5 carbon atoms or a fluorinated solvent.

* * * * *